(12) United States Patent
Ang et al.

(10) Patent No.: US 7,271,598 B1
(45) Date of Patent: Sep. 18, 2007

(54) CONDUCTOR COIL DEFECT IDENTIFIER

(75) Inventors: Kelvin Kor Seng Ang, Singapore (SG); Shaoyong Liu, Singapore (SG); Sivalingam Marimuthu, Singapore (SG); Yi Zhao Yao, Singapore (SG); Jingjing Zhang, Singapore (SG)

(73) Assignee: Hitachi Global Storage Technologies Netherlands, B.V., Amsterdam (NL)

( * ) Notice: Subject to any disclaimer, the term of this patent is extended or adjusted under 35 U.S.C. 154(b) by 0 days.

(21) Appl. No.: 11/478,000

(22) Filed: Jun. 28, 2006

(51) Int. Cl.
*G01R 31/02* (2006.01)

(52) U.S. Cl. ................................ 324/541; 324/551

(58) Field of Classification Search ............... 324/541, 324/551
See application file for complete search history.

(56) References Cited

U.S. PATENT DOCUMENTS

| | | | |
|---|---|---|---|
| 4,518,464 | A | 5/1985 | Takahashi et al. |
| 5,389,215 | A | 2/1995 | Horiuchi et al. |
| 5,750,257 | A | 5/1998 | Doshita et al. |
| 6,411,110 | B1 * | 6/2002 | Gilton ................. 324/718 |
| 6,524,965 | B2 | 2/2003 | Chen |
| 6,593,759 | B2 * | 7/2003 | Gilton ................. 324/718 |

FOREIGN PATENT DOCUMENTS

| | | |
|---|---|---|
| JP | 59155749 | 9/1984 |
| JP | 61018842 | 1/1986 |
| JP | 61-195467 | 12/1986 |
| JP | 1288758 | 11/1989 |
| JP | 1305348 | 12/1989 |
| JP | 3054445 | 3/1991 |
| JP | 6050927 | 2/1994 |
| JP | 10267884 | 10/1998 |
| JP | 2000088789 | 3/2000 |
| JP | 2003232766 | 8/2003 |
| WO | WO86/05881 | 10/1986 |

* cited by examiner

*Primary Examiner*—Walter Benson

(57) ABSTRACT

A system and method for detecting a defect in an actuator arm conductor coil is disclosed. An actuator arm including a conductor coil is received. The conductor coil is coupled with a voltage as an anode. The conductor coil is submerged into a first solution, the first solution having no organic matter therein. The first solution is then coupled with a second solution including an organic indicator. The second solution also includes a cathode coupled to the voltage such that a defect in an insulation layer of the conductor coil is indicated by the organic indicator.

20 Claims, 4 Drawing Sheets

CONDUCTOR COIL DEFECT IDENTIFIER

TECHNICAL FIELD

The present invention relates generally to defective insulation detection, and more particularly to a system and method for detecting a defect in an actuator arm conductor coil.

BACKGROUND ART

Hard disk drives are used in almost all computer system operations. In fact, most computing systems are not operational without some type of hard disk drive to store the most basic computing information such as the boot operation, the operating system, the applications, and the like. In general, the hard disk drive is a device which may or may not be removable, but without which the computing system will generally not operate.

The basic hard disk drive model includes a storage disk or hard disk that spins at a designed rotational speed. An actuator arm is utilized to reach out over the disk. The arm carries a head assembly that has a magnetic read/write transducer or head for reading/writing information to or from a location on the disk. The transducer is attached to a slider, such as an air-bearing slider, which is supported adjacent to the data surface of the disk by a cushion of air generated by the rotating disk. The transducer can also be attached to a contact-recording type slider. In either case, the slider is connected to the actuator arm by means of a suspension. The complete head assembly, e.g., the suspension and head, is called a head gimbal assembly (HGA).

In operation, the hard disk is rotated at a set speed via a spindle motor assembly having a central drive hub. Additionally, there are tracks evenly spaced at known intervals across the disk. When a request for a read of a specific portion or track is received, the hard disk aligns the head, via the arm, over the specific track location and the head reads the information from the disk. In the same manner, when a request for a write of a specific portion or track is received, the hard disk aligns the head, via the arm, over the specific track location and the head writes the information to the disk.

Over the years, the disk and the head have undergone great reductions in their size. Much of the refinement has been driven by consumer demand for smaller and more portable hard drives such as those used in personal digital assistants (PDAs), MP3 players, and the like. For example, the original hard disk drive had a disk diameter of 24 inches. Modern hard disk drives are much smaller and include disk diameters of less than 2.5 inches (micro drives are significantly smaller than that). Advances in magnetic recording are also primary reasons for the reduction in size.

However, this continual reduction in size has placed steadily increasing demands on quality control. For example, diligent inspection of hard disk drive components is essential to providing a high quality, reliable product.

One of the components in a hard disk drive which is important to inspect is the coil of wire used to form the conductor coil of the actuator arm that controls position of the read-write heads. Generally, the conductor coil is formed from a small diameter wire. The wire is generally made mostly of copper but also may be alloyed with other metals for improved strength. Normally, the wire is coated with an insulating sheath that is flexible enough to allow the wire to be shaped into a coil without undue damage to the insulation.

However, this insulation is subject to abrasion, cracking, pinholes or other degradation. The degradation can occur at any of the manufacturing stages of the wire including initial fabrication, coil winding, cleaning, up to and including final preparation and installation in the actuator arm. For example, during ultrasonic washing of the wire coil, erosion of the conductor itself can occur. In many cases, the erosion includes pinholes or other abrasions in the insulating coating. Failure to detect these defects prior to installation of the actuator arm in the hard disk drive can lead to hard disk drive failures.

Present methods exist for detecting insulated wire defects. However, as the insulated wire size is reduced, the present method is no longer able to detect the smallest abrasions or holes in the insulation. Moreover, the present testing method requires a testing sample that cannot rejoin the manufacturing process regardless of whether it passes or fails. For example, the present testing methods provide an organic solution on the insulation during the testing process. Because of the contamination of the organic matter with respect to the wire coils and the carriage assembly, after testing the test subject must be scrapped.

Thus, there is a need for a test method that is able to identify a small defect in the insulation while also permitting test components that are defect free to be returned to the manufacturing line and used in a functional hard disk drive.

SUMMARY

A system and method for detecting a defect in an actuator arm conductor coil is disclosed. An actuator arm including a conductor coil is received. The conductor coil is coupled with a voltage as an anode. The conductor coil is submerged into a first solution, the first solution having no organic matter therein. The first solution is then coupled with a second solution including an organic indicator. The second solution also includes a cathode coupled to the voltage such that a defect in an insulation layer of the conductor coil is indicated by the organic indicator.

DETAILED DESCRIPTION

Reference will now be made in detail to the alternative embodiment(s) of the present invention. While the invention will be described in conjunction with the alternative embodiment(s), it will be understood that they are not intended to limit the invention to these embodiments. On the contrary, the invention is intended to cover alternatives, modifications and equivalents, which may be included within the spirit and scope of the invention as defined by the appended claims.

Furthermore, in the following detailed description of the present invention, numerous specific details are set forth in order to provide a thorough understanding of the present invention. However, it will be recognized by one of ordinary skill in the art that the present invention may be practiced without these specific details. In other instances, well known methods, procedures, and components have not been described in detail as not to unnecessarily obscure aspects of the present invention.

The discussion will begin with an overview of a hard disk drive and components connected therewith. The discussion will then focus on an exemplary conductor coil and a physical description of the conductor coil defect identifier apparatus. Finally, an exemplary method for using the conductor coil defect identifier to test a conductor coil will be described.

Alternative methods described herein provide a conductor coil defect identifier that is able to sensitively detect defective conductor coils without removing a passing conductor coil from the manufacturing process. In other words, the defective conductor coil detection method and system described herein will identify defective conductor coils without detrimentally affecting non-defective conductor coils. Moreover, the defective conductor coil detector described herein has increased sensitivity for detection of pinhole size defects, decreases the detector test time and significantly reduces the waste solution generated during the testing when compared with present testing methods.

Overview

Figure 1:
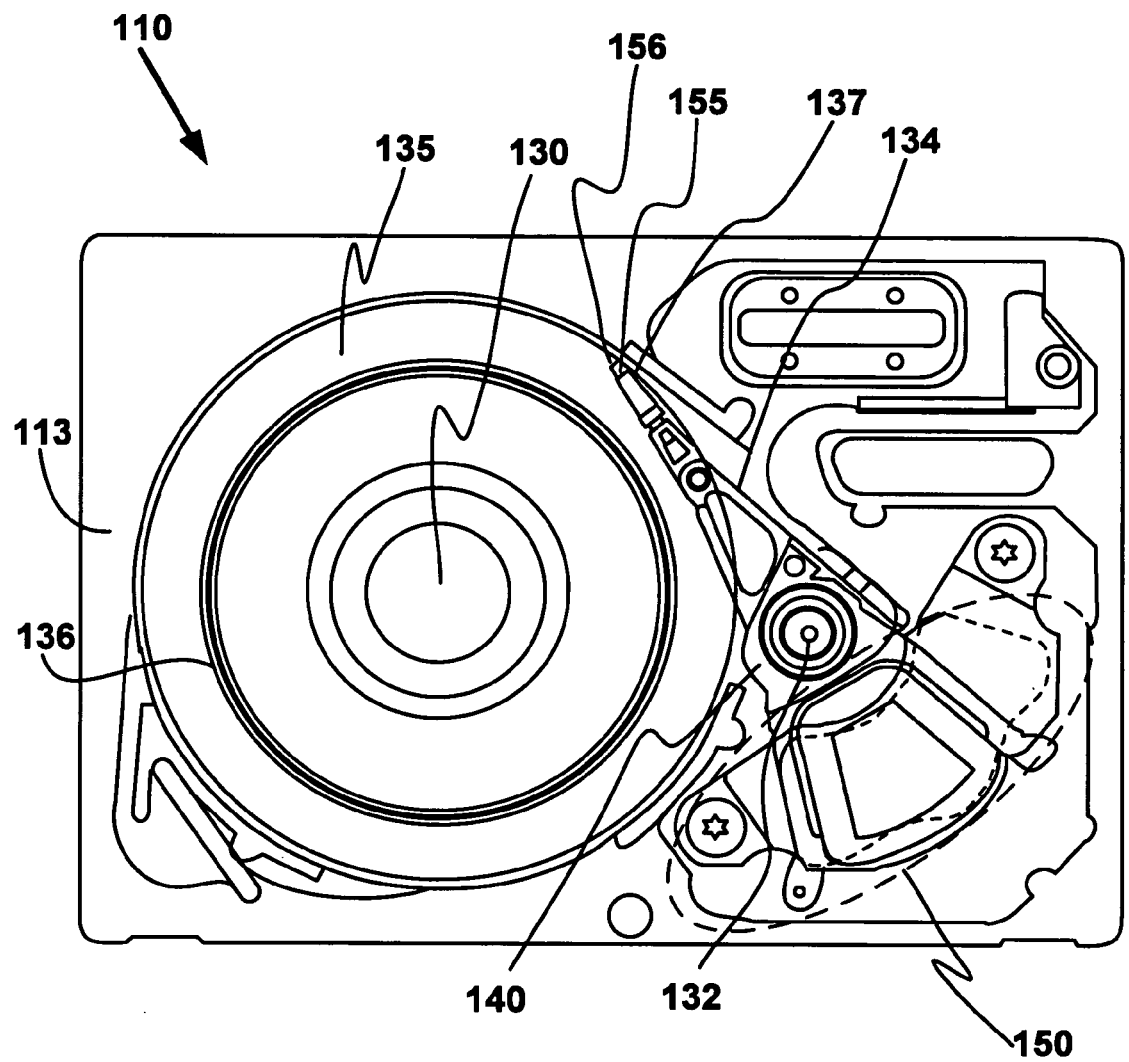
FIG. 1 is a plan view of an hard disk drive (HDD) with cover and top magnet removed in accordance with one embodiment of the present invention.

With reference now to FIG. 1, a plan view of an HDD with cover and top magnet removed is shown in accordance with one embodiment of the present invention. FIG. 1 illustrates the relationship of components and sub-assemblies of HDD 110 and a representation of data tracks 136 recorded on the disk surfaces 135 (one shown). The cover is removed and not shown so that the inside of HDD 110 is visible. The components are assembled into base casting 113, which provides attachment and registration points for components and sub-assemblies.

A plurality of suspension assemblies 137 (one shown) are attached to the actuator arms 134 (one shown) in the form of a comb. A plurality of transducer heads or sliders 155 (one shown) are attached respectively to the suspension assemblies 137. Sliders 155 are located proximate to the disk surfaces 135 for reading and writing data with magnetic heads 156 (one shown). The rotary voice coil motor 150 rotates actuator arms 134 about the actuator shaft 132 in order to move the suspension assemblies 150 to the desired radial position on disk surfaces 135. The actuator shaft 132, hub 140, actuator arms 134, and voice coil motor 150 may be referred to collectively as a rotary actuator assembly.

Data is recorded onto disk surfaces 135 in a pattern of concentric rings known as data tracks 136. Disk surface 135 is spun at high speed by means of a motor-hub assembly 130. Data tracks 136 are recorded onto spinning disk surfaces 135 by means of magnetic heads 156, which typically reside at the end of sliders 155. FIG. 1 being a plan view shows only one head, slider, and disk surface combination. One skilled in the art understands that what is described for one head-disk combination applies to multiple head-disk combinations, such as disk stacks (not shown). However, for purposes of brevity and clarity, FIG. 1 only shows one head and one disk surface.

Figure 2:
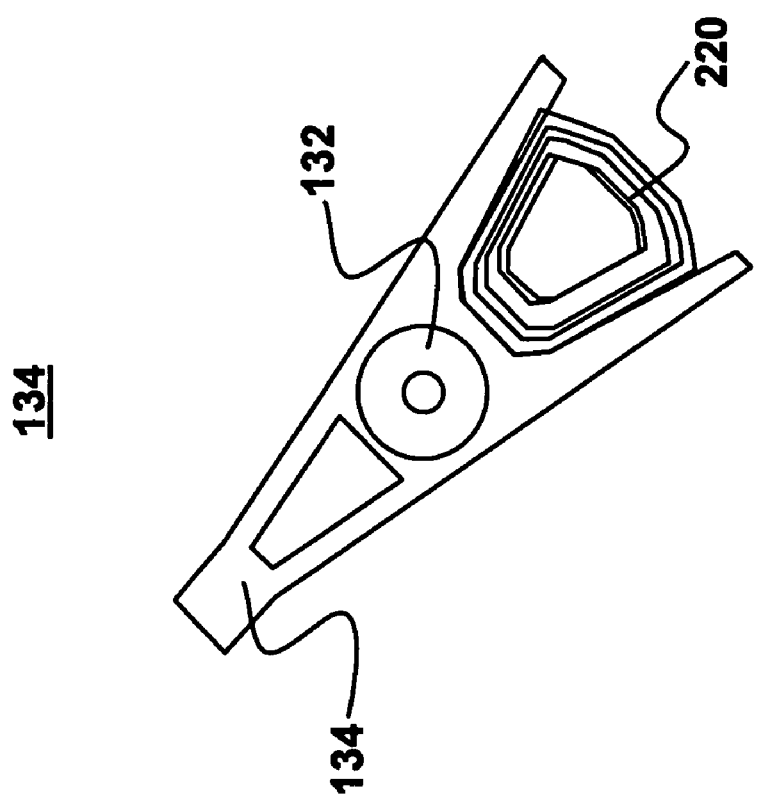
FIG. 2 is an exemplary plan view of an actuator arm with a conductor coil in accordance with one embodiment of the present invention.

Referring now to FIG. 2, an exemplary plan view of an actuator arm 134 with an actuator shaft 132 and a conductor coil 220 is shown in accordance with one embodiment. In general, the wire used to make the conductor coil 220 is formed from a small diameter wire. The wire is generally made mostly of copper but also may be alloyed with other metals for improved strength. Normally, the wire is coated with an insulating sheath that is flexible enough to allow the wire to be formed into a coil without undue damage to the insulation. In one exemplary embodiment, the conductor coil 220 is wound in a quasi-circle and fitted into a trough in the end of an actuator arm 134.

The fine diameter of the wire 220 makes it difficult to inspect with the naked eye for pinhole defects, or abrasions, or other such impairments. Such defects can lead to a cracked conductor that in turn leads to a failure of the hard disk drive. Other ways in which such defects may occur include a manufacturing failure from the wire vendor and erosion to the exposed section of wire while undergoing the ultrasonic washing process.

Figure 3:
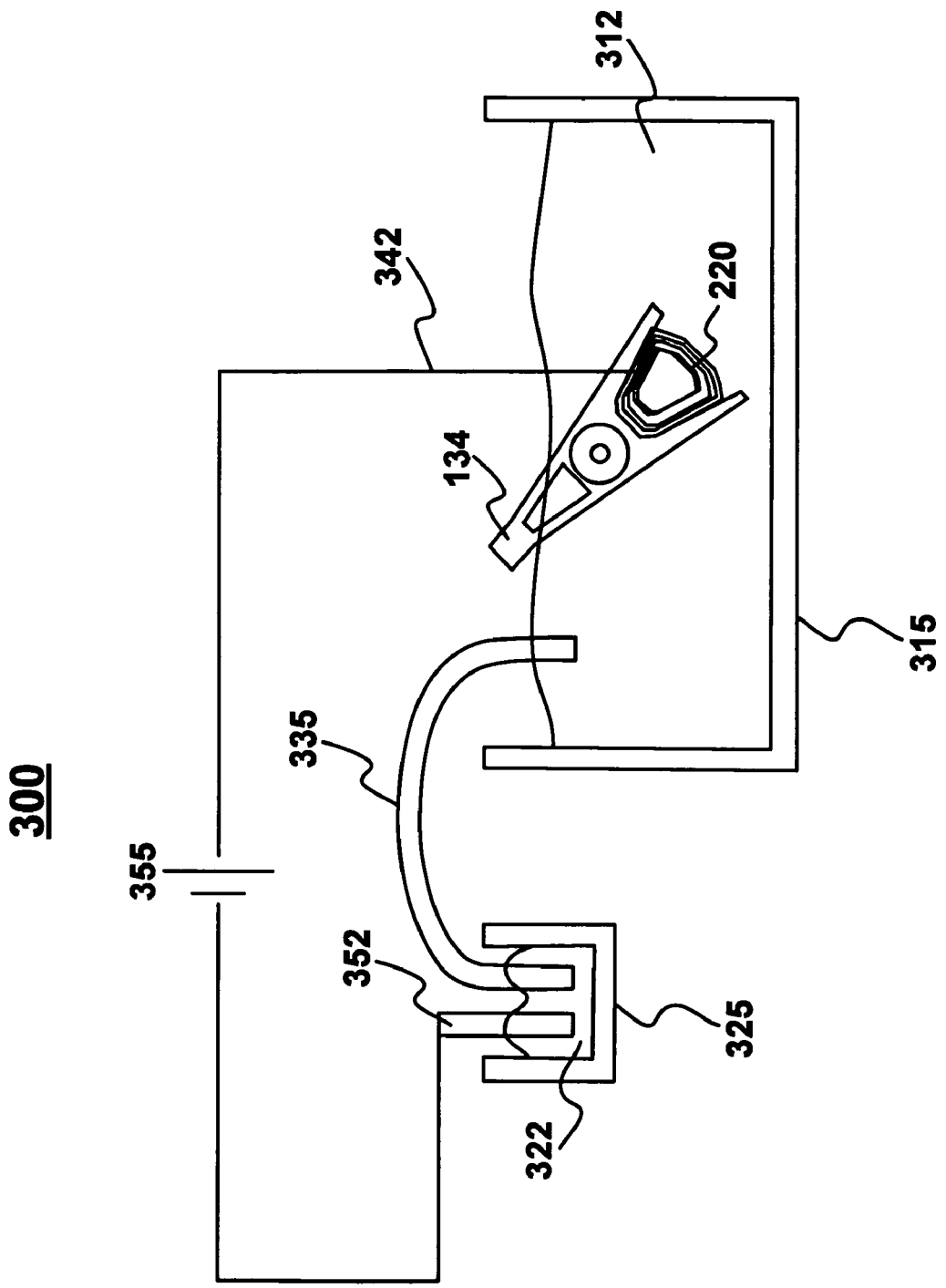
FIG. 3 is an exemplary conductor coil defect identifier in accordance with one embodiment of the present invention.

With reference now to FIG. 3, an exemplary conductor coil defect identifier 300 is shown in accordance with one embodiment of the present invention. In general, the test system 300 consists of a modified electrolysis cell. In one embodiment, the test system 300 includes a first container 315 having a first solution 312 and a second container 325 having a second solution 322. The test system 300 also includes a salt bridge 335, and a cathode 352. In one embodiment, the conductor coil 220 of the actuator arm 134 is suspended in the first solution 312 and is used as the anode in the system. A power source 355 is used to supply current to the circuit. In one embodiment, the power source 355 is a direct current (DC) power source, e.g., a battery, transformer or the like.

Operation

Figure 4:
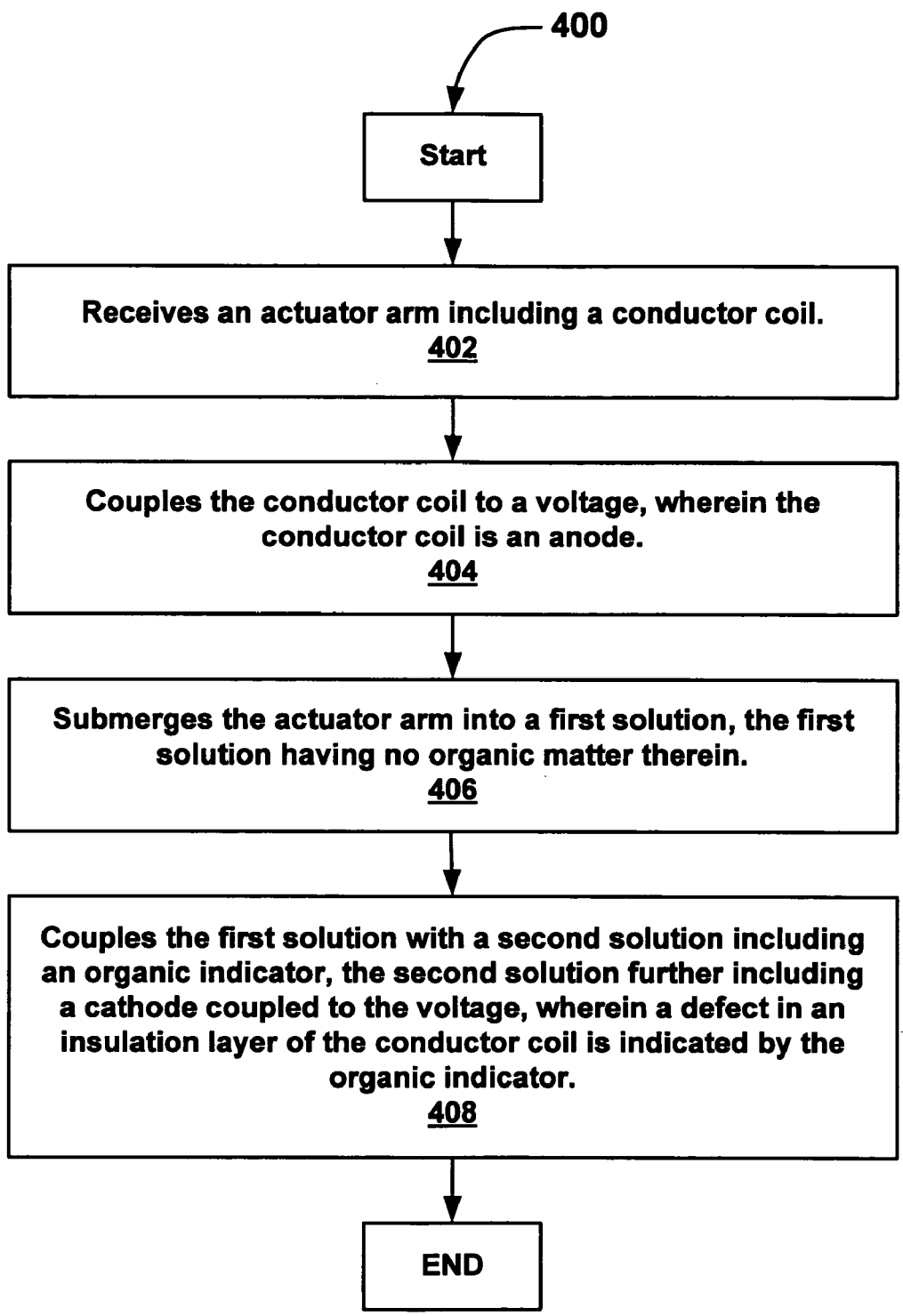
FIG. 4 is a flowchart of an exemplary method for detecting a defect in an actuator arm conductor coil in accordance with one embodiment of the present invention.

With reference now to FIG. 4, a flowchart 400 of an exemplary method for detecting a defect in an actuator arm conductor coil is shown in accordance with one embodiment. Unlike standard electrolysis cells presently used for insulation testing, in system 300 (of FIG. 3), the conductor coil 220 acts as the anode instead of the cathode. Also, the organic indicator is added to the cathode side thereby eliminating the potential for organic contamination of the coil. Additionally, the anode side and cathode side are separate but electrically coupled by a salt bridge. Because the organic indicator is no longer in the first test chamber holding the conductor coil, a surfactant can also be added to the anode side to reduce surface tension thereby increasing detection capabilities. Thus, unlike organic indicators, the surfactant can be easily removed in the washing process of the conductive coil. This easy wetting also increases the reaction process which significantly reduces test time.

Because the detector is in the cathode side 325 of the system 300 and is separate from the anode side 315 of the system, the amount of detector fluid 322 can be significantly reduced since the container 325 no longer needs to be large enough to contain the conductor coil 220. In other words, the indicator container 325 can contain a small amount such as, for example, 2 ml in volume with only enough room to hold the cathode 352. Therefore, when the indicator is worn out or otherwise needs replacement, the amount of waste solution is significantly reduced and the amount of new organic detector solution required is also significantly reduced.

With reference now to 402 of FIG. 4 and to FIG. 3, one embodiment receives an actuator arm 134 including a conductor coil 220. The actuator arm 134 is in one embodiment, a portion of a larger HDD assembly such as assembly 110 of FIG. 1. Moreover, the actuator arm 134 and conductor coil 220 may be new components that have yet to be assembled into a HDD 110 or may be components that are taken and tested from a previously assembled HDD 110.

Referring now to 404 of FIG. 4 and to FIG. 3, one embodiment, couples the conductor coil 220 to a voltage 355, wherein the conductor coil 220 is an anode. For example, in one embodiment, the conductor coil 220 is coupled via a conductive clip to the source of direct current (DC) electricity 355 via a wire conductor 342 to the exposed end of the conductor coil 220 acting as the anode.

With reference now to 406 of FIG. 4 and to FIG. 3, one embodiment submerges the conductor coil into a first solution having no organic matter therein. For example, in one embodiment, the conductor coil 220 is suspended in a first container 315 having a first solution 312 utilizing a conductive clip. However, the suspension may be realized in any number of well-known ways. Its function may also be performed by coupling the battery wire 342 directly to the coil 220 and suspending the coil 220 in the fluid 312 without utilizing a separate suspension mechanism. In one embodiment, the first solution is distilled water. In another embodiment, the first solution is an electrolyte solution.

Referring now to 408 of FIG. 4 and to FIG. 3, one embodiment couples the first solution 312 with a second solution 322 including an organic indicator. In one embodiment, the organic indicator is phenolphthalein. The second solution 322 in a second container 325 also including a cathode 352 coupled to the voltage 355, wherein a defect in an insulation layer of the conductor coil 220 is indicated by the organic indicator. In other words, the water-insoluble organic color indicator is now added to the second solution 322 instead of the first solution 312. The quantity of electrolyte and color indicator may be much smaller than what is required for immersion of the wire coil in the first electrolyte. For example, the amount of electrolyte can be as small as 2 ml.

Thus, by creating a second chamber 325 for fluid 322, it becomes possible to move the organic color indicator to the second chamber 325. As stated herein, the movement of the indicator will allow the fluid 312 containing the conductor coil 220 to be free of organic indicators. In so doing, organic contamination of the actuator arm 134 and conductor coil 220 is avoided.

Moreover, after removing the organic detector from the first solution 312, the surface tension of the first electrolyte solution 312 may be reduced by the addition of a wetting agent, often referred to as a surfactant. Common wetting agents include detergents and the like.

In one embodiment, a salt bridge 335 electrically couples the first fluid (e.g., electrolyte) 312 to the second fluid (e.g., electrolyte) 322 in a second chamber 325. The second chamber 325 includes a cathode 352 for completing the circuit to the source 355. Generally, the salt bridge 335 is an important component of the electrochemical defect identifier 300. This type of cell can produce an electric current as a product of a chemical reaction type known as oxidation-reduction (also known as redox). The cell reaction is divided into two parts: oxidation (electron loss) and reduction (electron gain). The salt bridge 335 exists to provide the electrical connection between the two reaction vessels (325 and 315) while keeping the two reactions separate. The salt bridge 335 allows the electron transfer between the two vessels.

In operation, the amount of current that flows through the system is governed by the insulation. For example, if the insulation is completely intact the resistance is high and no indication is shown in fluid 322. However, if the insulation is defective, the resistance is lowered to direct contact between the first electrolyte 312 and the wire conductor 220. In fact this resistance essentially drops to zero since the wire 220 is in direct contact with the electrolyte 312. When this resistance drops, enough current flows through the circuit 300 to activate the color indicator which changes color, thereby indicating the existence of a defect in the insulation.

Thus, embodiments of the present invention provide a system and method for detecting a defect in an actuator arm conductor coil. Moreover, embodiments provide a system and method for detecting a defect in an actuator arm conductor coil that significantly increases the detection capability allowing the detection of smaller defects. Additionally, embodiments for detecting a defect in an actuator arm conductor coil avoid introducing organic contamination during the testing process such that when a part is found non-defective, it can be returned to the production line thereby significantly reducing scrap rate and increasing cost savings. Furthermore, embodiments for detecting a defect in an actuator arm conductor coil described herein significantly reduce the amount of chemical solution used and replaced. In so doing, embodiments described herein provide an efficient, sensitive, economical and environmentally friendly method for detecting a defect in an actuator arm conductor coil.

While the method of the embodiment illustrated in flowchart 400 show specific sequences and quantity of steps, the present invention is suitable to alternative embodiments. For example, not all the steps provided for in the methods are required for the present invention. Furthermore, additional steps can be added to the steps presented in the present embodiment. Likewise, the sequences of steps can be modified depending upon the application.

The alternative embodiment(s) of the present invention, a system and method for detecting a defect in an actuator arm conductor coil is thus described. While the present invention has been described in particular embodiments, it should be appreciated that the present invention should not be construed as limited by such embodiments, but rather construed according to the below claims.

What is claimed is:

1. A method for detecting a defect in an actuator arm conductor coil, said method comprising:
   receiving an actuator arm comprising a conductor coil;
   coupling said conductor coil to a voltage, wherein said conductor coil is an anode;
   submerging said conductor coil into a first solution, said first solution having no organic matter therein; and
   coupling said first solution with a second solution comprising an organic indicator, said second solution further comprising a cathode coupled to said voltage, wherein a defect in an insulation layer of said conductor coil is indicated by said organic indicator.

2. The method of claim 1 further comprising:
providing a salt bridge for coupling said first solution with said second solution.

3. The method of claim 1 further comprising:
utilizing distilled water as said first solution.

4. The method of claim 3 further comprising:
providing a surfactant in said first solution.

5. The method of claim 4 further comprising:
utilizing said surfactant to reduce the surface tension of said first solution to increase defect detection sensitivity.

6. The method of claim 1 further comprising:
utilizing a volume of approximately 2 ml for said second solution having said organic indicator therein.

7. The method of claim 1 further comprising:
utilizing phenolphthalein as said organic indicator.

8. A conductor coil defect identifier comprising:
a first solution for submerging said conductor coil of an actuator arm, said first solution having no organic properties;
a second solution having an organic indicator therein, said second solution distinct from said first solution;
a salt bridge for conductively coupling said first solution and said second solution; and
a voltage source coupled with said conductor coil in said first solution and a cathode in said second solution, wherein any defects in an insulation layer above said conductor coil will produce an indication in said organic indicator.

9. The conductor coil defect identifier of claim 8 wherein said first solution comprises distilled water.

10. The conductor coil defect identifier of claim 9 wherein said first solution further comprises a surfactant.

11. The conductor coil defect identifier of claim 10 wherein said surfactant reduces the surface tension in said first solution to increase defect detection sensitivity.

12. The conductor coil defect identifier of claim 8 wherein said second solution having said organic indicator therein is approximately 2 ml in volume.

13. The conductor coil defect identifier of claim 8 wherein said organic indicator is phenolphthalein.

14. A method for detecting a defect in an actuator arm conductor coil of a hard disk drive, said method comprising:
receiving an actuator arm of a hard disk drive, said actuator arm comprising a conductor coil;
coupling said conductor coil to a voltage source, wherein said conductor coil is an anode;
submerging said at least said conductor coil of said actuator arm into a first solution, said first solution having no organic matter therein;
providing a second solution comprising an organic indicator and a cathode coupled to said voltage; and
coupling said first solution and said second solution with a salt bridge such that said first solution is distinct from said second solution, wherein a defect in an insulation layer of said conductor coil in said first solution is indicated by said organic indicator in said second solution.

15. The method of claim 14 further comprising:
utilizing distilled water as said first solution.

16. The method of claim 15 further comprising:
providing a surfactant in said first solution.

17. The method of claim 16 further comprising:
utilizing said surfactant to reduce the surface tension of said first solution to increase defect detection sensitivity.

18. The method of claim 14 further comprising:
utilizing a volume of approximately 2 ml for said second solution having said organic indicator therein.

19. The method of claim 14 further comprising:
utilizing phenolphthalein as said organic indicator.

20. A means for detecting an actuator arm conductor coil defect comprising:
a means for submerging a conductor coil of an actuator arm, said means for submerging a conductor coil having no organic properties;
an indicator means distinct from said means for submerging a conductor coil;
a conductor means for conductively coupling said means for submerging a conductor coil and said indicator means; and
a voltage means for providing a voltage between said means for submerging a conductor coil and said indicator means, wherein any defects in an insulation layer of said conductor coil will produce an indication in said indicator means when said voltage means is applied.

* * * * *